(12) United States Patent
Misch

(10) Patent No.: US 8,430,669 B2
(45) Date of Patent: Apr. 30, 2013

(54) METHOD FOR PREPARING AN IMPLANT SITE AND LATERALLY INSERTING A DENTAL IMPLANT

(76) Inventor: Carl E. Misch, Birmingham, MI (US)

( * ) Notice: Subject to any disclaimer, the term of this patent is extended or adjusted under 35 U.S.C. 154(b) by 0 days.

(21) Appl. No.: 13/401,080

(22) Filed: Feb. 21, 2012

(65) Prior Publication Data

US 2013/0045461 A1    Feb. 21, 2013

(51) Int. Cl.
*A61C 8/00* (2006.01)

(52) U.S. Cl.
USPC .................................. 433/176; 433/119

(58) Field of Classification Search .................. 433/119, 433/173, 176
See application file for complete search history.

(56) References Cited

U.S. PATENT DOCUMENTS

| | | |
|---|---|---|
| 3,919,772 A | 11/1975 | Lenczycki |
| 3,925,892 A | 12/1975 | Juillet |
| 4,516,937 A | 5/1985 | Bosker |
| 4,722,687 A | 2/1988 | Scortecci |
| 4,789,337 A | 12/1988 | Scortecci |
| 4,815,974 A | 3/1989 | Scortecci |
| 4,842,517 A | 6/1989 | Kawahara et al. |
| 4,964,801 A | 10/1990 | Kawahara et al. |
| 5,306,149 A | 4/1994 | Schmid et al. |
| 5,312,256 A | 5/1994 | Scortecci |
| 5,320,529 A | 6/1994 | Pompa |
| 5,433,607 A | 7/1995 | Schmid et al. |
| 5,927,979 A | 7/1999 | Misch |
| 6,068,480 A | 5/2000 | Misch |
| 6,083,004 A | 7/2000 | Misch |
| 6,402,516 B2 | 6/2002 | Ihde |
| 6,695,847 B2 | 2/2004 | Bianchetti et al. |
| 6,899,715 B1 * | 5/2005 | Beaty .............................. 606/80 |
| 6,991,463 B2 | 1/2006 | Ihde |
| 7,691,106 B2 | 4/2010 | Schenberger et al. |
| 7,758,344 B2 * | 7/2010 | Gogarnoiu .................... 433/166 |
| 8,002,783 B2 | 8/2011 | Vercellotti et al. |
| 8,118,597 B2 * | 2/2012 | Misch ........................... 433/176 |
| 8,241,037 B2 * | 8/2012 | Ihde .............................. 433/176 |
| 8,277,220 B2 * | 10/2012 | Spahn ........................... 433/176 |
| 2007/0015102 A1 * | 1/2007 | Vercellotti et al. ................. 433/2 |
| 2009/0326440 A1 | 12/2009 | Lee |
| 2010/0167235 A1 | 7/2010 | Vercellotti et al. |
| 2010/0240009 A1 * | 9/2010 | Gogarnoiu .................... 433/173 |

FOREIGN PATENT DOCUMENTS

| | | |
|---|---|---|
| EP | 0 935 949 A1 | 8/1999 |
| FR | 2 302 715 | 10/1976 |

OTHER PUBLICATIONS www.piezosurgery.com, Mectron Medical Technology, Piezosurgery, downloaded Oct. 4, 2010, pp. 1-12.

* cited by examiner

*Primary Examiner* — Ralph Lewis
(74) *Attorney, Agent, or Firm* — Brooks Kushman P.C.

(57) ABSTRACT

A method of positioning a dental implant in a jaw bone using a piezoelectric cutting tool is provided. Ultrasonic vibration is generated with the piezoelectric cutting tool. The piezoelectric cutting tool is translated in a lateral direction to form a first cut into the jaw bone and to form a second cut into the jaw bone. The second cut intersects the first cut to define a multi-slotted aperture in the jaw bone for receiving at least one dental implant. The dental implant is inserted in the multi-slotted aperture from the lateral direction.

20 Claims, 6 Drawing Sheets

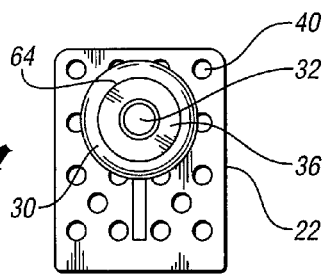
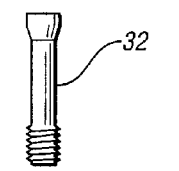 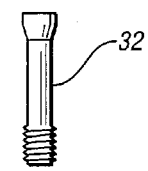 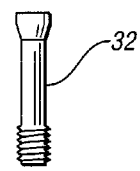
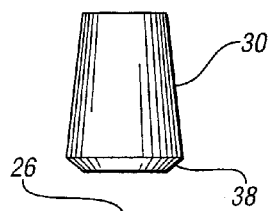 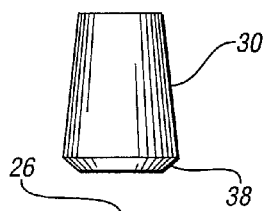 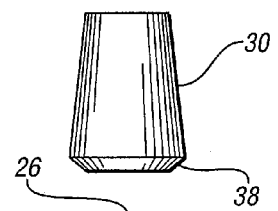
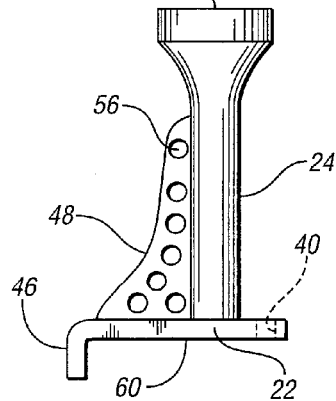 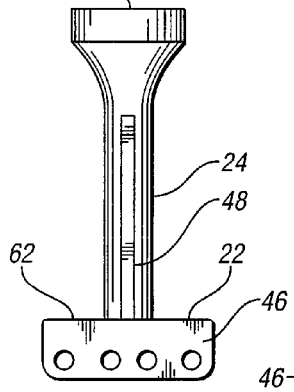 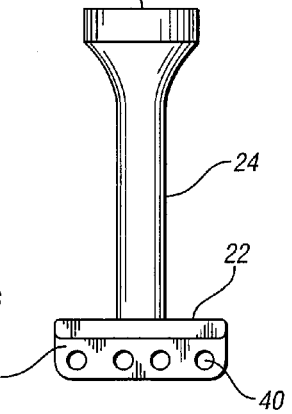
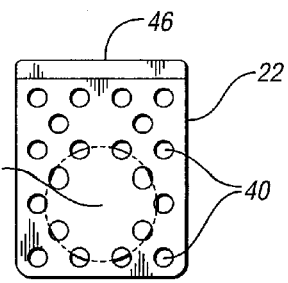

METHOD FOR PREPARING AN IMPLANT SITE AND LATERALLY INSERTING A DENTAL IMPLANT

TECHNICAL FIELD

The invention relates to a method of surgically implanting a laterally inserted dental implant assembly that is placed surgically within the mandibular or maxillary bone to support and provide resistance to displacement of a dental prosthesis, its method of implantation, and a related kit that includes a cutting tool and an implant assembly.

BACKGROUND

Modern dentistry recognizes that functions of the masticatory system are best achieved by conserving and protecting remaining hard and soft tissues. For some patients, the loss of even a few teeth is traumatic. There is a strong incentive to seek dental care to preserve and restore normal speech, masticatory function, and a socially acceptable appearance. Dental implants have been developed in response to these needs.

Implant-supported fixed prostheses offer several advantages: avoidance of soft-tissue and implant trauma avoidance of bone complications caused by implant mobilization during mastication optimum fit at the bone-implant interface since the bone adapts immediately after implant placement and subsequent installation of the fixed prosthetic tooth. Such implants have been known to function well under various physiological conditions—normal food intake, which helps the body and peri-implant tissues to heal faster, stimulation of blood supply and drainage: avoidance of venous stasis, normal speech and resumption of socio-professional activities, and increased patient self-confidence.

But post-type implants and the way they are positioned have drawbacks. The boring of the bone in a vertical plane is necessarily deep to accommodate the height of the implant. But the bone may not have sufficient height. Also, the implant cannot easily pass round such obstacles as sinuses, nasal fossae, nerves, because boring is almost always done vertically.

Moreover, such implants, when inserted vertically are subject to the transmission of the forces imposed on them by mastication. They work essentially on an edge and have a strong tendency to self-bore under chewing or tooth-grinding pressures. Consequently these types of known post-type implants cannot be adapted to all bony structures.

In positioning a dental implant, it is desirable to seat the implant securely into the bone. Even the slightest mobility of the implant inside the bone often leads to ultimate rejection.

Conventionally, once the implant is set into the bone, a tapped ring or screw is set onto the outside part of the implant, which is generally a threaded rod. Onto this tapped ring or screw, a dental prosthesis is fixed, usually with a cement.

With a laterally inserted dental implant, osteotomy is initiated on the buccal or lingual/palatal aspect of the jaw. (Scortecci, Mich et al., "Implants and restorative dentistry", p. 5 (2001).) Such implants are exemplified by the T3D implant developed by Juillet (1972) and the Diskimplant® (Scortecci, 1984). The Diskimplant® requires a specific instrument for osteotomy—a cutter manufactured of titanium. The Diskimplant® combines a horizontal disk and a post. See, e.g., U.S. Pat. No. 4,789,337, which is incorporated herein by reference.

A cutting tool may be used to prepare the lateral bone incision from one cortical layer to the other. The minimally larger implant is then impacted into the bone receptor site. Close contact at the bone-implant interface encourages immediate primary retention. A wide range of base diameters and column heights allows the surgeon to make optimal use of all available bone in both horizontal and vertical dimensions.

One advantage of such approaches is that the placement of laterally inserted implants eliminates the need for reduction of thin premaxillary ridges, in contrast to conventional screw-type implants. Subsequent crestal bone loss and gingival retraction are thus less severe and often nonexistent. As a result, a better aesthetic outcome is achieved without systematic grafting.

Such disk-column implants represent a possible solution for patients with small bone volumes. The technique can also be used to salvage situations in which an implant and/or graft have failed. Stresses are concentrated primarily at the base of the disk.

However, one of the weaknesses of conventional disk-column systems, is that the column or post that lies in the center of the disk and is relatively small in diameter. Not infrequently, fracture of the implant is often the result. Such implants, inserted in a lateral direction often break under the stresses imposed during insertion or in use. One problem of conventional approaches is that the post is often too facial to the natural tooth position in the mandible and too palatal in the maxilla.

A related problem with conventional disk-column techniques is that if the hole is oversized, or if the underlying bone is soft, the implant is not fixed securely after insertion.

The prior art is also exemplified by U.S. Pat. Nos. 4,722,687 and 4,815,974.

SUMMARY

In one protocol, a method of preparing a jaw bone for receiving a dental implant a dental implant is provided. The method includes generating an ultrasonic vibration with a cutting tool. The cutting tool is translated tool in a lateral direction to form a first cut into the jaw bone; and translated in the lateral direction to form a second cut into the jaw bone. The second cut intersects the first cut to define a multi-slotted aperture for receiving the dental implant.

In another protocol, the first cut is substantially orthogonal to the second cut.

In yet another protocol, the first cut forms a generally horizontal aperture and the second cut forms a generally vertical aperture.

In a further protocol, the multi-slotted aperture is defined as a T-shaped aperture.

In another protocol, the cutting tool is translated in the lateral direction form a third cut into the bone. The third cut intersects at least one of the first and second cuts.

In a further protocol, the dental implant is inserted into the multi-slotted aperture. The dental implant includes a base plate, a ledge extending therefrom from a first face of the base plate, a pillar extending therefrom from a second face of the baseplate, and a planar buttress that extends between the base plate and the pillar.

In one other protocol, a method of preparing a jaw bone for receiving a dental implant with a piezoelectric cutting tool is provided. The piezoelectric cutting tool generates ultrasonic vibration. The piezoelectric cutting tool is translated in a lateral direction to form a cut into the jaw bone. The cut is defined as a T-shaped aperture in the bone as the piezoelectric cutting tool translates in the lateral direction.

In another protocol, the piezoelectric cutting tool includes a linear cutting tip.

In yet another protocol, the T-shaped aperture is defined by a first cut to form one of a horizontal aperture and vertical aperture, and a second cut to form the other of the horizontal and vertical apertures.

In a further protocol, a dimension of the linear cutting tip is substantially equal to a dimension of the horizontal or vertical apertures.

In one further protocol, a method of positioning a dental implant in a jaw bone using a piezoelectric cutting tool is provided. Ultrasonic vibration is generated with the piezoelectric cutting tool. The piezoelectric cutting tool is translated in a lateral direction to form a first cut into the jaw bone and to form a second cut into the jaw bone. The second cut intersects the first cut to define a multi-slotted aperture in the jaw bone for receiving at least one dental implant. The dental implant is inserted in the multi-slotted aperture from the lateral direction.

In another protocol, the dental implant is inserted laterally into the multi-slotted aperture so that a base plate is inserted in the first cut and a post is inserted into the second cut.

In a further protocol, the base plate has a first bone-facing surface and a second pillar-supporting surface that defines an off-center region. The dental implant includes a ledge depending from the first bone-facing surface of the base plate away from the second pillar-supporting surface at an angle theta. A pillar extends from the off-center region of the pillar-supporting surface of the base plate. A planar buttress extending between the pillar-supporting surface of the base plate and the pillar for strengthening a connection therebetween.

BRIEF DESCRIPTION OF THE DRAWINGS

FIGS. 4(a)-(e) respectively represent top plan, left, front, rear and bottom plan views of the implant assembly depicted in FIG. 3;

DETAILED DESCRIPTION

As required, detailed embodiments of the present invention are disclosed herein; however, it is to be understood that the disclosed embodiments are merely examples of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

The invention includes a surgical protocol for preparing an anchoring site for an endo-osseous anatomic dental implant assembly and its insertion process.

Figure 1:
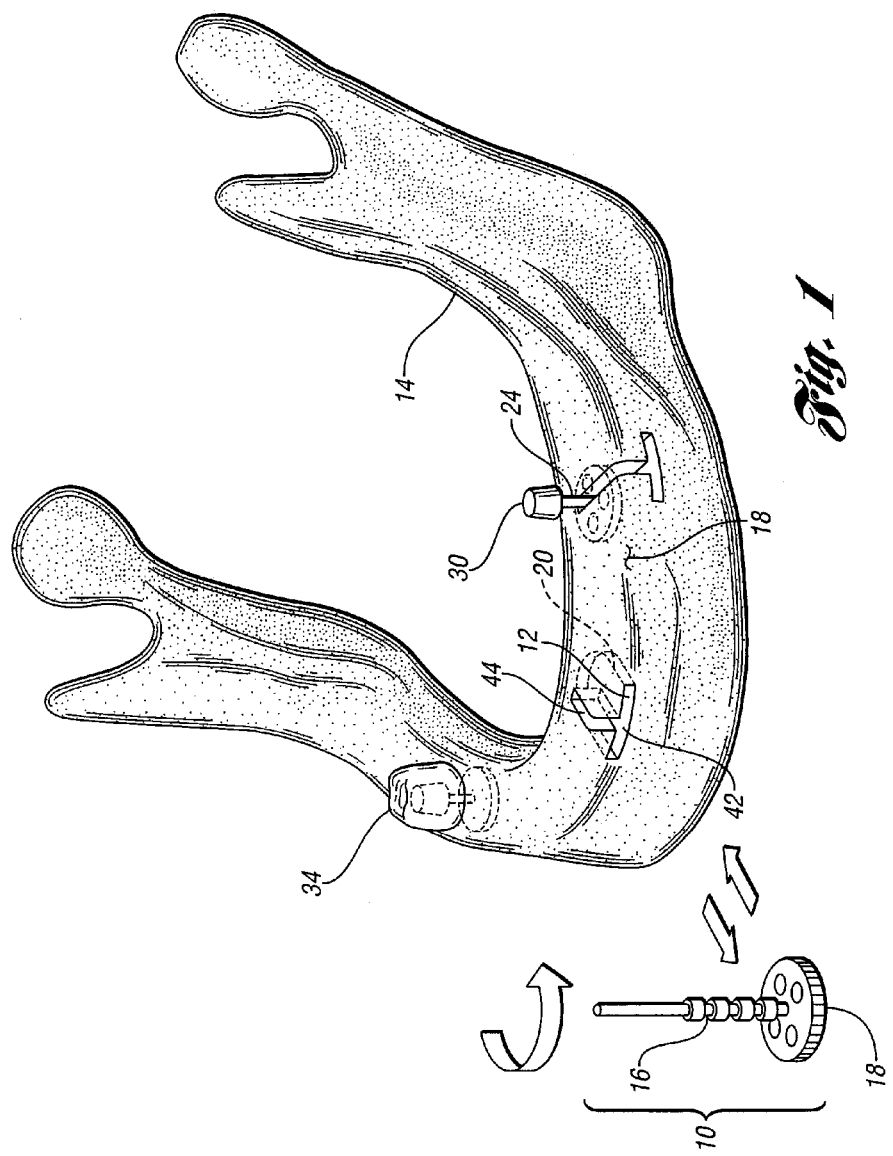
FIG. 1 is a perspective view of a lower jaw showing positioned implants, with their posts ready to receive a dental prosthesis, a representative rotary cutting tool in operation, and an anchoring site for receiving the implant.
Figure 8:
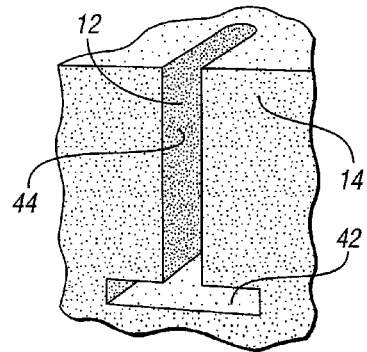
FIG. 8 depicts a slot and a tunnel of an anchoring site defined in the bone which corresponds to the profile generated by the rotary cutting tool used in accordance with the disclosed protocol.

FIG. 1 depicts representative embodiments of an implant and a schematic representation of a cutting action associated with the invention. Energized by a rotating drill, for example, a rotary cutting tool 10 prepares the implant site 12 in a bone, such as a lower jaw bone 14 that receives the implant. The rotary cutting tool 10 includes a stem 16 that is used as a milling cutter and a disk 18 extending perpendicularly to the longitudinal axis of the stem 16. Thus, the stem 16 of the rotary cutting tool 10 cuts the substantially vertically aligned slot 44 of the implant site 12, while the disk 18 defines the tunnel 42 of the implant site 12 (see also, FIG. 8).

In another embodiment of the disclosure, a vibratory cutting tool 70, such as a piezoelectric cutting tool, may be employed to prepare the implant site 12 in the bone. The vibratory cutting tool 70 and method are discussed in greater detail below with regard to FIGS. 9 & 10.

Figures 2, 3:
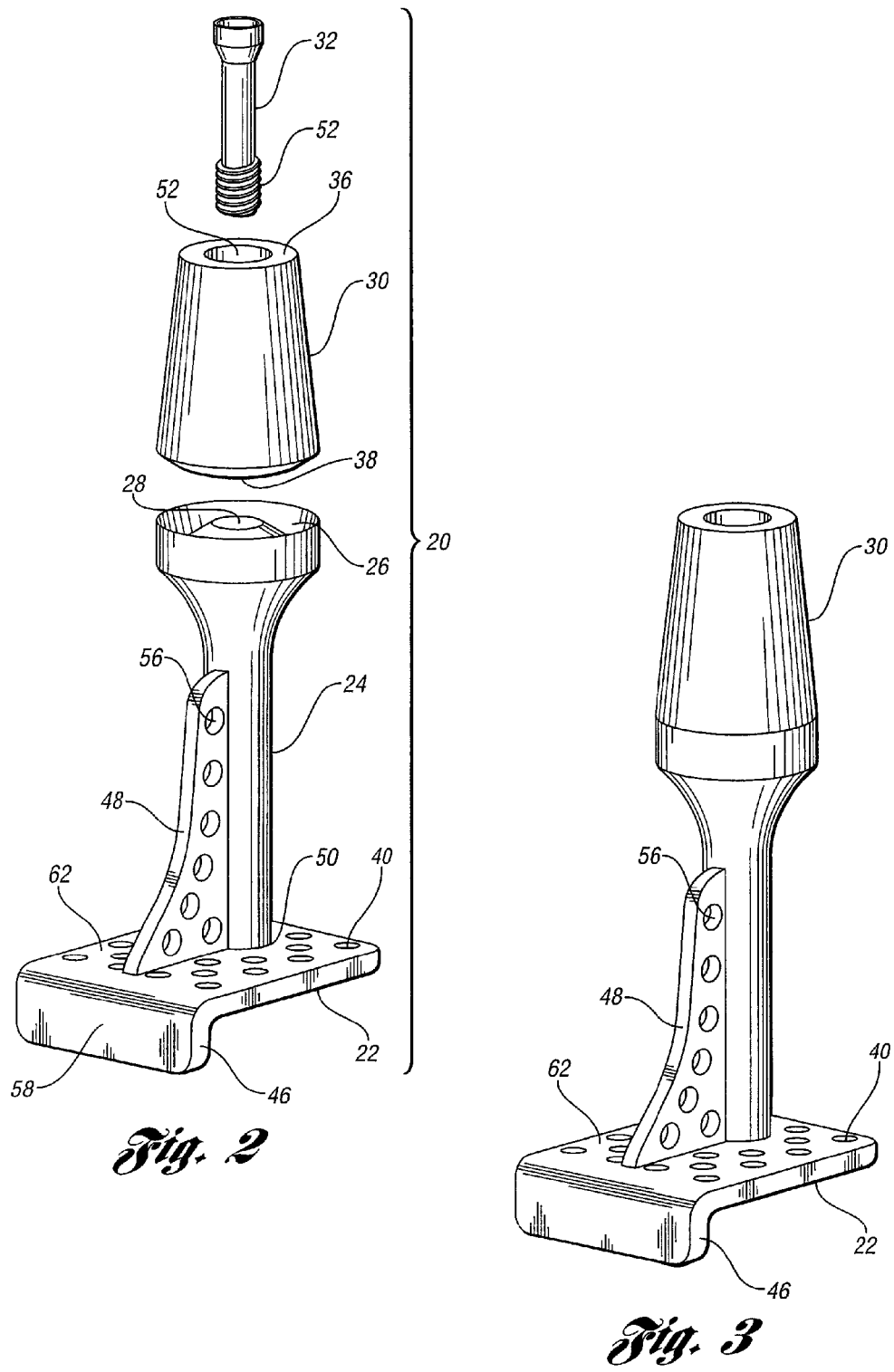
FIG. 2 is an exploded perspective view of a laterally inserted dental implant assembly for securing a dental prosthesis according to one embodiment of the disclosure.
FIG. 3 depicts the dental implant assembly in its conjoined form, ready to receive the dental prosthesis.

FIGS. 2-4 depict an implant assembly 20 constructed in accordance with one embodiment of the invention. The assembly 20 has a base 22 that is preferably substantially perpendicular to the longitudinal axis of a pillar 24. The base 22 has a bone-facing surface 60 a pillar supporting surface 62, and an off-center region 64 (FIG. 4). At the opposite or distal end 26 of the pillar 24 there is a receiving device 28 which accommodates a tapped body 30 and with a through bore or a threaded post 32 on which the dental prosthesis is positioned.

As best seen in FIGS. 2 & 4, the tapped body 30 in one embodiment is defined by two truncated conical surfaces 30, 38. Major frustoconical portion 36 has a threaded post-receiving aperture that receives the threaded post 32 for supporting the tooth or the prosthetic superstructure. Minor frustoconical portion 38 has a through bore. It is contiguous with the gum and shaped to allow the gum tissue to assume the contours of its circumference. This limits the risks of irritation and retention of the bacterial plaque and food remains. The minor frustoconical portion 38 suppresses any overhanging and thus the blocks of such unwanted substances.

The base 22 of the implant assembly 20 may have multiple apertures 40 which can accommodate locking screws (not shown) to reduce the weight of the material of the implant without impairing its mechanical characteristics. Osseous tissue grows through the implant base 22 via these apertures 40 and contributes to biological blocking provided by osseous imprisonment of the base 22, the buttress 48 and the pillar 24.

In FIGS. 2-4 & 6-7 there is depicted a ledge 46 that depends downwardly by an angle theta that is preferably perpendicular to the base plate 22. If desired, apertures 58 or locking holes can be provided through the ledge 46 through which screws or pins can be inserted to secure the plate to the bone. Thus, the implant assembly 20 can be immobilized, and healing is thereby promoted.

FIGS. 2, 3, 4(a) & 6-7 illustrate that in one embodiment, the pillar 24 is located in an off-center region 64 in relation to the base plate 22. When the ledge 46 abuts the bone, the pillar 24 is able to be placed more inwardly than is possible with prior approaches. One benefit of such relocation is that the opposite distal end 26 of the pillar 24 may more closely underlie a ridge of the bone and therefore be more strongly supported.

Preferably, the buttress 48 is provided between the pillar 24 and the base plate 22, as depicted in FIGS. 2, 3, 4(a), 4(b), 4(c), 6 & 7. The buttress 48 may guide the implant assembly 20 during lateral insertion, contribute additional anchoring surfaces for bone growth, and provide mechanical support to the base plate 22 and pillar 24, thereby prolonging the useful life of the implant assembly 20.

Figure 5:
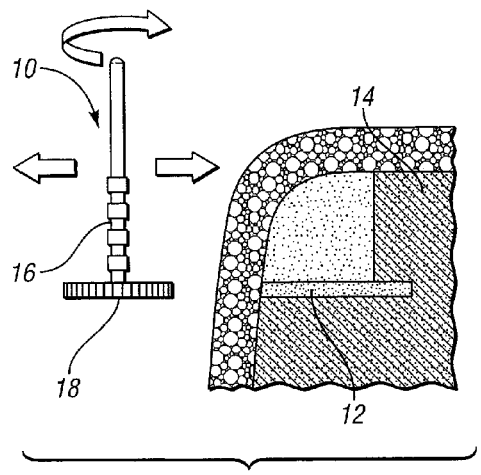
FIG. 5 shows how a rotary cutting tool can go into and out of an anchoring site defined by a tunnel and a slot for the implant before insertion of the implant laterally into the site created by the cutting tool.
Figure 6:
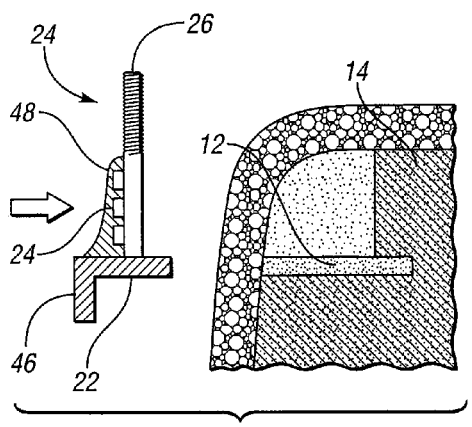
FIG. 6 depicts an implant about to be pressed into its seating tunnel and slot. The implant plate and pillar are preferably wider respectively than the slot and tunnel defined by the cutting tool, which ensures a firm grip of the implant when seated.
Figure 7:
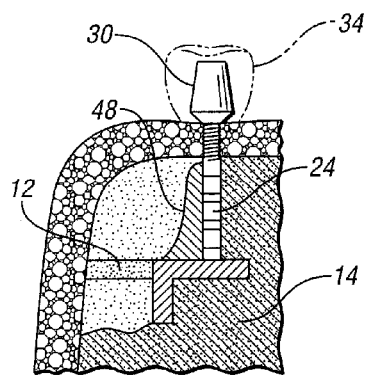
FIG. 7 is a schematic view of one embodiment of the implant in situ. A distal end of the implant pillar is equipped with a tapped body which allows a dental prosthesis to be threadingly secured or cemented thereupon.

FIG. 5 illustrates a representative cutting action of one type of rotary cutting tool 10 into the bone to define an implant site 12 for receiving the implant assembly 20. This implant site 12 corresponds to the profile projected laterally of the assembly 20 to be inserted generally horizontally into the implant site 12. Only the end 26 of pillar 24 (FIG. 6) opposite the base 22 protrudes from the edge of bone 14. FIG. 7 shows implant assembly 20 in position, firmly supporting a prosthesis 34 after the pillar 24 has been selected for the required height and has received the corresponding tapped body 30.

The base plate 22 that supports the axially extending pillar 24 is in one embodiment a quadrilateral or other polygon or disk that after insertion lies mainly disposed in a horizontal plane. In one embodiment, this plate 22 is shaped so as to be set into the mandibula or the maxilla by having side edges that are oriented on converging lines, thereby permitting a wedging interference fit upon insertion.

In use, the base plate 22 is inserted into a tunnel 42 (FIG. 8) made in the vestibular, lingual or palatal side of a bone. The pillar 24 is inserted into a slot 44—a passage that intersects the plane of the tunnel 42.

When placing the implant assembly 20 laterally against a bony wall, the practitioner, in a straight-line translation movement, allows intra- and trans-osseous penetration of the base plate 22 in a plane parallel to that of the cutting disk 18. He inserts the pillar 24 and buttress 48 in an intersecting plane that is rigidly connected to the base plate 22.

Preferably, the implant assembly 20, to be positioned correctly, has a profile that is slightly larger than the rotary cutting tool 10 in order to permit an interference fit into the formed tunnel 42 and slot 44.

Thus, the implant assembly 20, is placed in the tunnel 42 and slot 44 formed by the rotary cutting tool 10. The implant assembly 20 is inserted laterally into the implant site 12 preferably on the vestibular side so that only the distal end 26 of the pillar 24 opposite the base plate 22 protrudes from the bone edge (FIG. 7). The pillar 24 is selected according to the required height to receive the threaded post 32 or tapped body 30. Before its final biological blocking by regeneration of the bone around the implant assembly 20, the implant assembly 20 is stable.

In one embodiment, one aspect of the implant assembly 20 is identical to that of the rotary cutting tool 10. Others may be thicker to avoid any mobility of the implant assembly 20 in its seated position.

Preferably, the base 22 has a smooth edge instead of being indented or grooved. The pillar 24 can be either smooth or grooved.

Thus, the implant assembly 20 according to the invention includes pillar 24 with at a distal end 26 a smooth part that interfaces with the tapped body 30 which allows threaded post 32 to be secured thereto. At the other end of the pillar 24, least one base plate 22 is placed, preferably perpendicularly to the longitudinal axis of the pillar 24.

The invention solves several problems of prior approaches. It tends to ensure a faultless primary fixation owing to the precision with which the implant is cut into the bone. The implant assembly is generally made of a metal or metallic alloy. Thus, the implant assembly 20 can be used as an artificial root in the replacement of the missing natural dental pillars.

Figure 9:
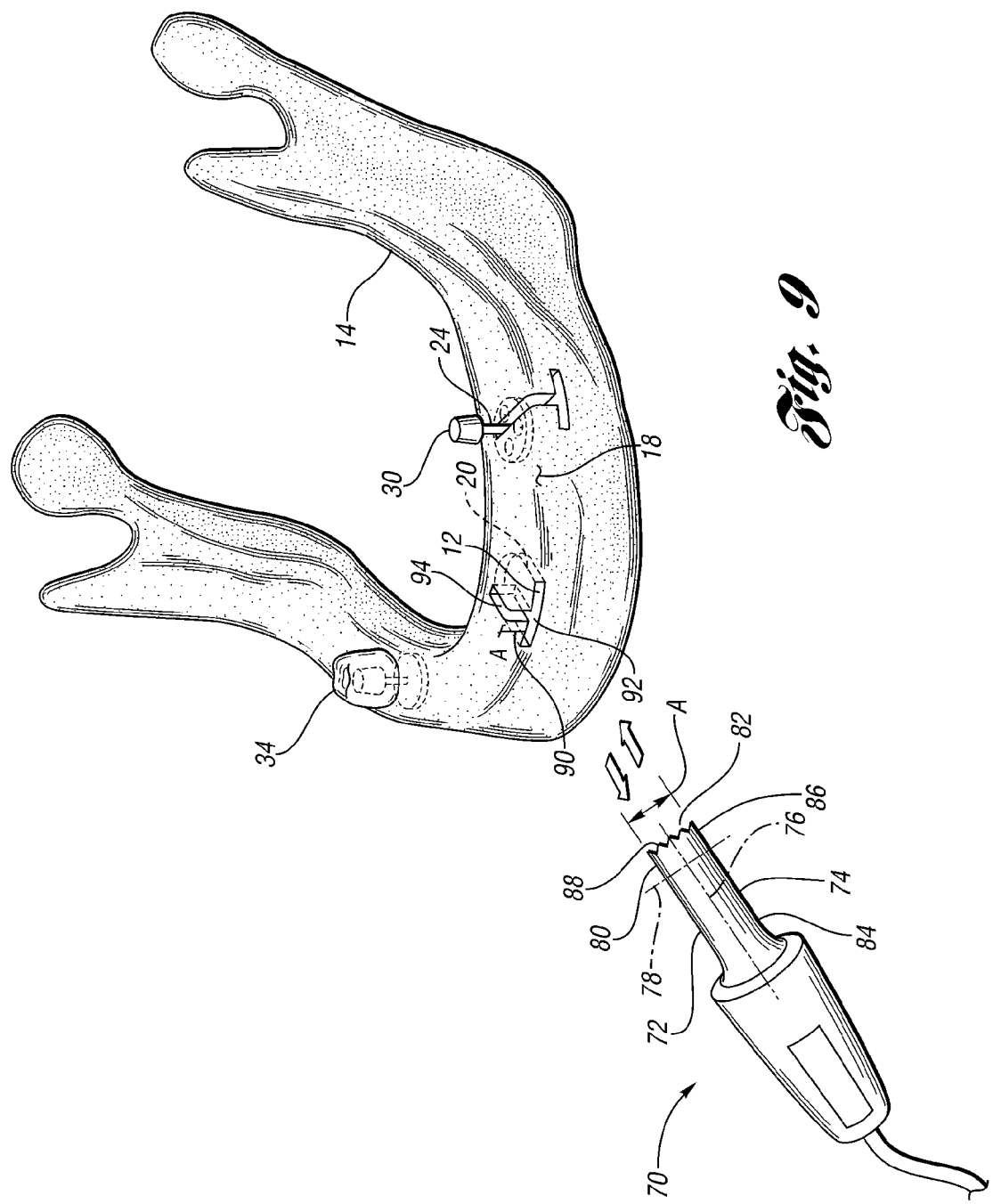
FIG. 9 is a perspective view of a vibratory cutting tool according to an alternate protocol, and an anchoring site in a lower jaw formed by the vibratory cutting tool for receiving the implant.

FIG. 9 illustrates a perspective view of a vibratory saw or cutting tool 70 according to an alternate embodiment of the invention. The vibratory cutting tool 70 may use piezoelectric technology using ultrasonic vibrations with a blade 72 having a precise design to prepare the implant site 12 for a dental implant assembly 20.

The vibratory cutting tool 70 generates sound waves that are transmitted to vibrate the blade 72. The blade 72 vibrates at a frequency within the sonic or ultrasonic range, such as 25 kHz to 30 kHz, or any suitable sonic or ultrasonic frequency to generate microvibrations. The vibratory cutting tool 70 may also modulate the vibration of the blade 72 in short pulses, bursts or lower frequencies. Alternatively, the vibratory cutting tool 70 may provide continuous ultrasonic vibration.

The vibratory cutting tool 70 has the advantage of a precise osteotomy in three-dimensions. The sonic or ultrasonic vibrations of the blade 72 define a very precise and fine cut in the jaw bone. This in turn has the advantage of reduced surgical trauma to surrounding soft tissues such as the cheeks, lips and nerves because of the precise control of the vibratory cutting tool 70. Further, in the event the blade 72 contacts any soft tissues, the sonic or ultrasonic vibrations may be absorbed by the soft tissue, minimizing the cutting capacity of the vibratory cutting tool 70 and causing minimal trauma to the soft tissue.

In one embodiment, the blade 72 includes an elongated body 74 having a longitudinal axis 76 and a transverse axis 78. A distal end 80 of the blade 72 may include a cutting portion 82. The blade 72 may also include an attachment portion 84 for attaching to the vibratory cutting tool 70. In the embodiment illustrated in FIG. 9, the attachment portion 84 is an extension of the elongated body 74. The attachment portion 84 may also be an alternate shape, such as a curved or angled portion so that cutting portion 82 is offset from the vibratory cutting tool 70. In another embodiment, the attachment portion 84 and blade 72 may be integral with the vibratory cutting tool 70.

As illustrated in FIG. 9, the cutting portion 82 is a linear cutting tip 86 defined substantially parallel to the transverse axis 78. The linear cutting tip 86 may include a plurality of serrated teeth 88 along the cutting portion 82. In other embodiments, the linear cutting tip 86 may be diamond coated or have another suitable cutting profile. Alternatively, the cutting portion 82 may be a pointed tip or any other suitable cutting configuration. The vibratory cutting tool 70 may provide sonic or ultrasonic vibration in a direction parallel to the transverse axis 78.

The vibratory cutting tool 70 may be used to prepare the implant site 12 in the jaw bone. As shown in FIG. 9, the implant site 12 is a multi-slotted aperture 90 for receiving the dental implant assembly 20. The multi-slotted aperture 90 may be defined by at least two apertures. In the illustrated embodiment, the multi-slotted aperture 90 has a generally horizontal aperture 92 and a generally vertical aperture 94. The horizontal aperture 92 and the vertical aperture 94 are generally orthogonal to each other. The multi-slotted aperture 90 may be formed at generally T-shaped, as shown, or may be any other suitable shape to receive a corresponding dental implant. The dimension A of the cutting portion may be substantially equal to a dimension of the horizontal or vertical apertures.

Figure 10:
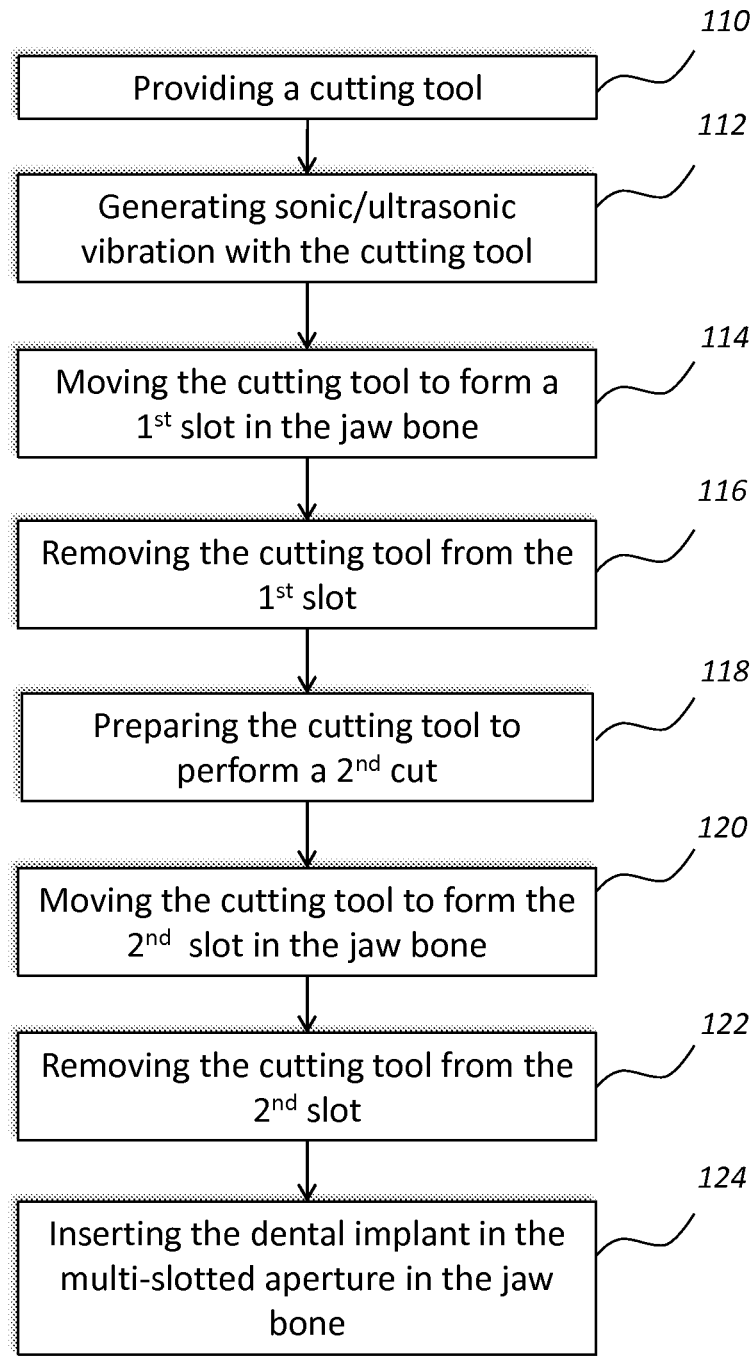
FIG. 10 is a flowchart illustrating the method of forming the anchoring site with a cutting tool according to one protocol.

FIG. 10 describes a method 100 for preparing a jawbone for a dental implant. First, the vibratory cutting tool 70 is provided, as represented by block 110. The vibratory cutting tool 70 generates a sonic or ultrasonic vibration, as represented by block 112.

The vibratory cutting tool 70 is translated in a lateral direction to form a first cut into the jaw bone, as represented by block 114. The lateral direction may be substantially parallel to the longitudinal axis of the blade 72. The vibratory cutting tool 70 is then withdrawn from the first cut, as represented by block 116.

The vibratory cutting tool 70 is prepared to perform a second cut, as represented by block 118. The vibratory cutting tool 70 may prepare for the second cut by being moved to a new location by rotating the vibratory cutting tool 70 at an angle about the longitudinal axis 76, or moving the vibratory cutting tool 70 in a linear direction, or any combination thereof. As shown in FIG. 9, the vibratory cutting tool 70 may be rotated approximately 90 degrees and moved so that the first cut is substantially orthogonal to the second cut and forms a T-shape.

A second cut into the jaw bone is be defined by translating the cutting tool in the lateral direction, as represented by block 120. The second cut intersects the first cut to define the multi-slotted aperture 90. The vibratory cutting tool 70 is withdrawn from the second cut, as represented by block 122.

In another embodiment, the vibratory cutting tool 70 may be prepared to form a third cut into the jawbone. The third cut may intersect at least one of the first and second cuts. It is also contemplated that any number of cuts may be used to define the multi-slotted aperture 90. For example, the T-shaped aperture illustrated may be formed by three or more cuts, such as two horizontal cuts and a vertical cut.

The dental implant assembly 20 is inserted laterally into the multi-slotted aperture 90 so that the base plate is inserted in the horizontal aperture and the post is inserted into the vertical aperture.

Here are the reference numerals used and the features to which they refer.

| Reference No. | Feature |
| --- | --- |
| 10 | Cutting Tool (rotary) |
| 12 | Site |
| 14 | Lower jaw bone |
| 16 | Stem of cutting tool |
| 18 | Disk |
| 20 | Implant assembly |
| 22 | Base plate |
| 24 | Pillar |
| 26 | Opposite (distal) end |
| 28 | Receiving device |
| 30 | Tapped body |
| 32 | Threaded post |
| 34 | Prosthesis post |
| 36 | Major frustoconical portion |
| 38 | Minor frustoconical portion |
| 40 | Apertures (in base) |
| 42 | Tunnel |
| 44 | Slot |
| 46 | Ledge |
| 48 | Buttress |
| 50 | Foot portion (of pillar) |
| 52 | Post receiving aperture (of 36) |
| 54 | Threaded region (of 52) |
| 56 | Apertures (in buttress) |
| 58 | Apertures (in ledge) |
| 60 | Bone-facing surface (of 22) |
| 62 | Pillar-supporting surface (of 22) |
| 64 | Off-center region (of 22) |
| 70 | Cutting tool (vibratory or piezoelectric) |
| 72 | Blade |
| 74 | Elongated body |
| 76 | Longitudinal axis |
| 78 | Transverse axis |
| 80 | Distal end (of blade) |
| 82 | Cutting portion |
| 84 | Attachment portion |
| 86 | Linear cutting tip |
| 88 | Teeth |
| 90 | Multi-slotted aperture |
| 92 | Horizontal aperture |
| 94 | Vertical aperture |

While various embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method of preparing a jaw bone for receiving a dental implant, the method comprising:
    generating ultrasonic vibration with a cutting tool;
    translating the cutting tool in a lateral direction to form a first cut into the jaw bone; and
    translating the cutting tool in the lateral direction to form a second cut into the jaw bone,
    wherein the second cut intersects the first cut to define a multi-slotted aperture for receiving the dental implant.

2. The method according to claim 1 wherein the cutting tool is a piezoelectric cutting tool.

3. The method according to claim 1 wherein the first cut is substantially orthogonal to the second cut.

4. The method according to claim 1 further comprising defining the first cut as a generally horizontal aperture and defining the second cut as a generally vertical aperture.

5. The method according to claim 1 wherein the slotted aperture is further defined as a T-shaped aperture.

6. The method according to claim 1 further comprising:
    withdrawing the cutting tool from the first cut; and
    rotating the cutting tool at an angle to define the second cut.

7. The method according to claim 1 further comprising translating the cutting tool to form a third cut into the bone, the third cut intersecting at least one of the first and second cuts.

8. The method according to claim 1 further comprising inserting the dental implant into the multi-slotted aperture, the dental implant including base plate, a ledge extending therefrom from a first face thereof, a pillar extending therefrom from a second face thereof and a planar buttress that extends between the base plate and the pillar.

9. A method of preparing a jaw bone for receiving a dental implant, the method comprising:
    providing an piezoelectric cutting tool;

generating ultrasonic vibration with the piezoelectric cutting tool;
translating the piezoelectric cutting tool in a lateral direction to form a cut into the jaw bone; and
defining the cut as a T-shaped aperture in the bone as the piezoelectric cutting tool translates in the lateral direction into the jaw bone.

10. The method according to claim 9 wherein the step of defining the T-shaped aperture further comprises:
defining a horizontal aperture with the piezoelectric cutting tool;
withdrawing the piezoelectric cutting tool from the horizontal aperture;
translating the piezoelectric cutting tool in the lateral direction to form a second cut into the jaw bone; and
defining the second cut as a vertical aperture to intersect the horizontal aperture.

11. The method according to claim 10 wherein the piezoelectric cutting tool includes a linear cutting tip; and
the method further comprising rotating the cutting tip by about 90 degrees to in order to define the second cut.

12. The method according to claim 11 wherein a dimension of the linear cutting tip is substantially equal to a dimension of one of the horizontal and vertical apertures.

13. The method according to claim 9 further comprising inserting the dental implant into the T-shaped aperture, the dental implant including a base plate, a pillar extending therefrom, and a planar buttress that extends between the base plate and the pillar.

14. A method of positioning a dental implant in a jaw bone, the method comprising:
providing a piezoelectric cutting tool;
generating ultrasonic vibration with the a piezoelectric cutting tool;
translating the piezoelectric cutting tool in a lateral direction to form a first cut into the jaw bone; and
translating the piezoelectric cutting tool in the lateral direction to form a second cut into the jaw bone, wherein the second cut intersects the first cut to define a multi-slotted aperture in the jaw bone for receiving at least one dental implant; and
inserting the dental implant in the multi-slotted aperture from the lateral direction.

15. The method according to claim 14 wherein the first cut is substantially orthogonal to the second cut.

16. The method according to claim 14 further comprising defining the first cut as a generally horizontal aperture and defining the second cut as a generally vertical aperture.

17. The method according to claim 14 further comprising inserting the dental implant laterally into the multi-slotted aperture so that a base plate is inserted in the first cut and a post is inserted into the second cut.

18. The method according to claim 17 wherein the base plate having a first bone-facing surface and a second pillar-supporting surface that defines an off-center region; the dental implant further including:
a ledge depending from the first bone-facing surface of the base plate away from the second pillar-supporting surface at an angle theta; and
a pillar extending from the off-center region of the pillar-supporting surface of the base plate; and
a planar buttress extending between the pillar-supporting surface of the base plate and the pillar for strengthening a connection therebetween.

19. The method according to claim 14 wherein the multi-slotted aperture is further defined as a T-shaped aperture.

20. The method according to claim 14 further comprising:
withdrawing the piezoelectric cutting tool from the first cut; and
rotating the cutting tool at an angle define the second cut.

* * * * *